(12) United States Patent
Veatch

(10) Patent No.: US 9,474,630 B2
(45) Date of Patent: Oct. 25, 2016

(54) JOINT AND DIGIT

(71) Applicant: Invisible Hand Enterprises, LLC, Westminster, CO (US)

(72) Inventor: Bradley Delton Veatch, Westminster, CO (US)

(73) Assignee: Invisible Hand Enterprises, LLC, Westminster, CO (US)

( * ) Notice: Subject to any disclaimer, the term of this patent is extended or adjusted under 35 U.S.C. 154(b) by 48 days.

(21) Appl. No.: 14/205,997

(22) Filed: Mar. 12, 2014

(65) Prior Publication Data

US 2014/0277589 A1    Sep. 18, 2014

Related U.S. Application Data

(60) Provisional application No. 61/777,024, filed on Mar. 12, 2013.

(51) Int. Cl.
| | |
|---|---|
| *A61F 2/58* | (2006.01) |
| *A61F 2/68* | (2006.01) |
| *A61F 2/50* | (2006.01) |

(52) U.S. Cl.
CPC ............... *A61F 2/586* (2013.01); *A61F 2/583* (2013.01); *A61F 2/68* (2013.01); *A61F 2002/5093* (2013.01)

(58) Field of Classification Search
CPC .......... A61F 2/54; A61F 2/583; A61F 2/586; A61F 2002/5016; A61F 2002/5038; A61F 2002/5039; A61F 2002/5041; A61F 2002/5043; A61F 2002/5093; A61F 2002/5095; A61F 2002/5096; A61F 2002/5098; A61F 2005/0134; A61F 2005/0137; A61F 2005/0146; A61F 2005/0148; A61F 2005/0151; A61F 2005/0153; A61F 2005/0132; A61F 5/013; A61F 2/4606; A61F 2/08; A61F 2002/0852; A61F 2002/0864; A61F 2002/0894; A61H 3/46; A61B 17/7291; Y10T 403/32008

See application file for complete search history.

(56) References Cited

U.S. PATENT DOCUMENTS

| | | | | | |
|---|---|---|---|---|---|
| 39,578 | A | * | 8/1863 | Kimball | 623/57 |
| 1,267,121 | A | * | 5/1918 | Sakowski | 623/63 |
| 1,324,564 | A | * | 12/1919 | Pringle | 623/64 |
| 1,608,689 | A | | 11/1926 | Apel | |
| 1,742,269 | A | | 1/1930 | McElroy | |
| 2,334,486 | A | * | 11/1943 | Froehlig | 446/363 |
| 2,500,614 | A | | 3/1950 | Lohmann | |
| 2,549,074 | A | | 4/1951 | Fishbein et al. | |

(Continued)

FOREIGN PATENT DOCUMENTS

| | | | | |
|---|---|---|---|---|
| WO | WO 2008030419 A2 | * | 3/2008 | A61F 2/54 |

OTHER PUBLICATIONS

Derwent abstract of DE19925479A1. Dechert, Alexander. Dec. 2000. Germany.*
Yrvind (1-3). Spars—a place for everything and everything in its place. (blog) Dec. 16, 2009.*
Needle. Experimental Dollmaking. (blog) May 9, 2008.*
Carlson, Lawrence. Spectron 12 Cable for Upper-Limb Prostheses. JPO 1991. vol. 3, No. 3, p. 130.*

(Continued)

*Primary Examiner* — Thomas J Sweet
*Assistant Examiner* — Christie Bahena
(74) *Attorney, Agent, or Firm* — Michael A. McIntyre

(57) ABSTRACT

This disclosure relates to the field of prosthetics, more specifically to a pinless anthropomorphic hinge or joint, and a digit comprising one or more phalanges connected by and articulating around pinless joints, whereby the joints provide compliant movement in more than one plane. This disclosure also relates to modular prosthetic systems comprising multiple digits, in particular for partial-hand replacements.

8 Claims, 12 Drawing Sheets

(56) References Cited

U.S. PATENT DOCUMENTS

| | | | | |
|---|---|---|---|---|
| 2,598,781 | A | * | 6/1952 | Gerbaud .................. 446/380 |
| 4,193,139 | A | | 3/1980 | Walker |
| 4,944,758 | A | | 7/1990 | Bekki et al. |
| 5,326,369 | A | | 7/1994 | Schectman |
| 7,361,197 | B2 | | 4/2008 | Winfrey |
| 7,655,051 | B2 | | 2/2010 | Stark |
| 2004/0054424 | A1 | | 3/2004 | Matsuda |
| 2006/0212129 | A1 | | 9/2006 | Lake et al. |
| 2006/0224249 | A1 | * | 10/2006 | Winfrey .................. 623/64 |
| 2012/0203358 | A1 | | 8/2012 | Lind et al. |

OTHER PUBLICATIONS

Yrvind (1-3). Spars—a place for everything and everything in its place. (Blog). Dec. 16, 2009. URL: www.yrvind.com/present_project/?p=31.*

Needle. Experimental Dollmaking. (blog) May 9, 2008. URL: https://needleandclay.wordpress.com/2008/05/09/experimental-dollmaking/.*

Pauline. Button Jointing for Beginners. Funky friends factory. Sep. 14, 2010. URL: www.funkyfriendsfactory.com/blog/button-jointing-for-beginners/.*

* cited by examiner

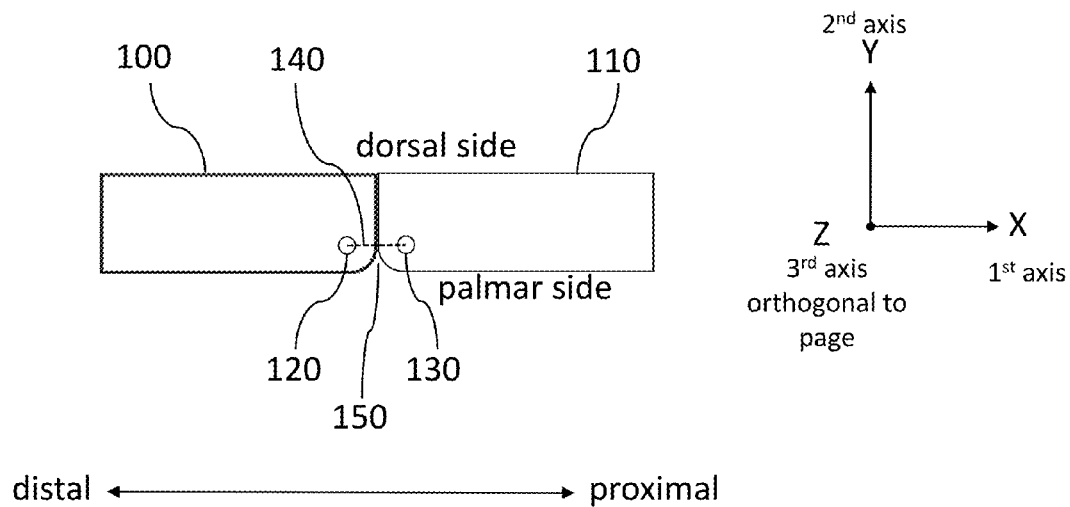
Figure 1 (mid-sagittal view)
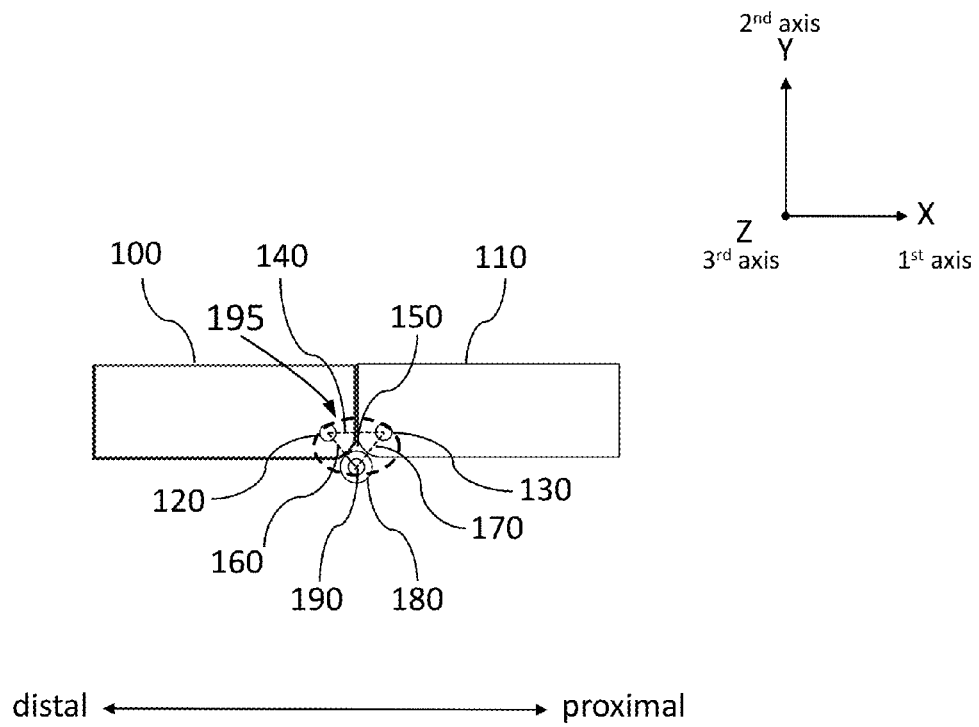
Figure 2 (mid-sagittal view)

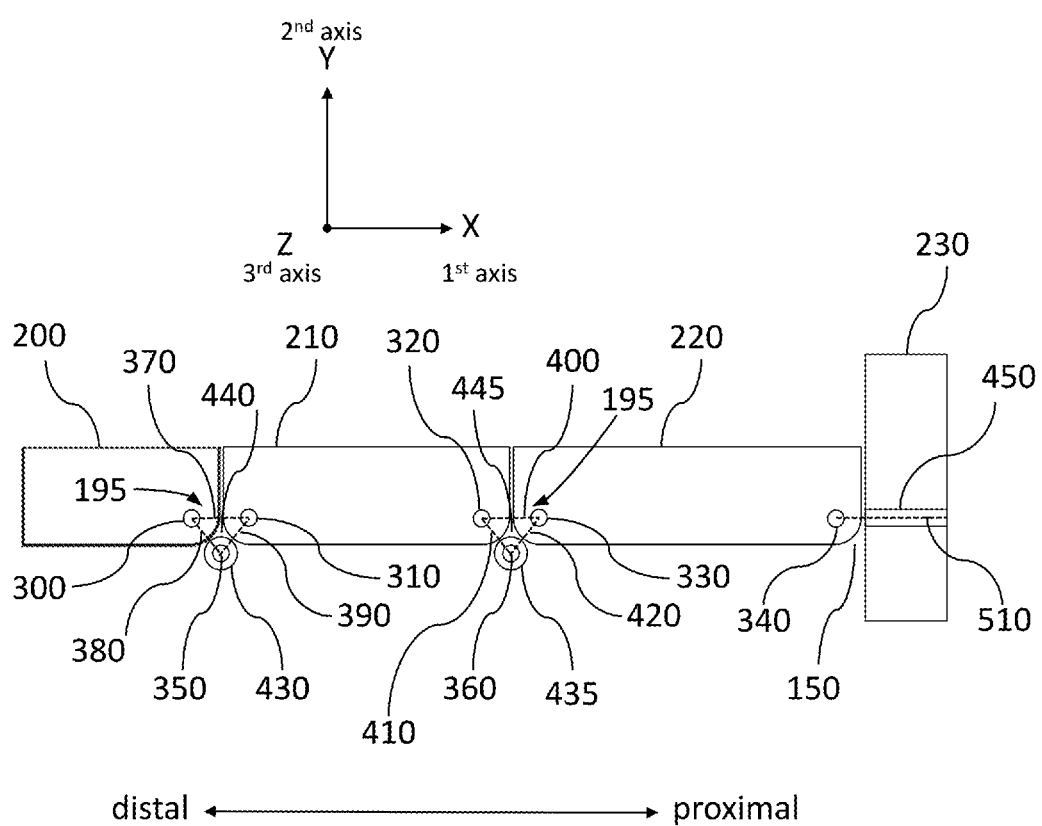
Figure 3 (mid-sagittal view)

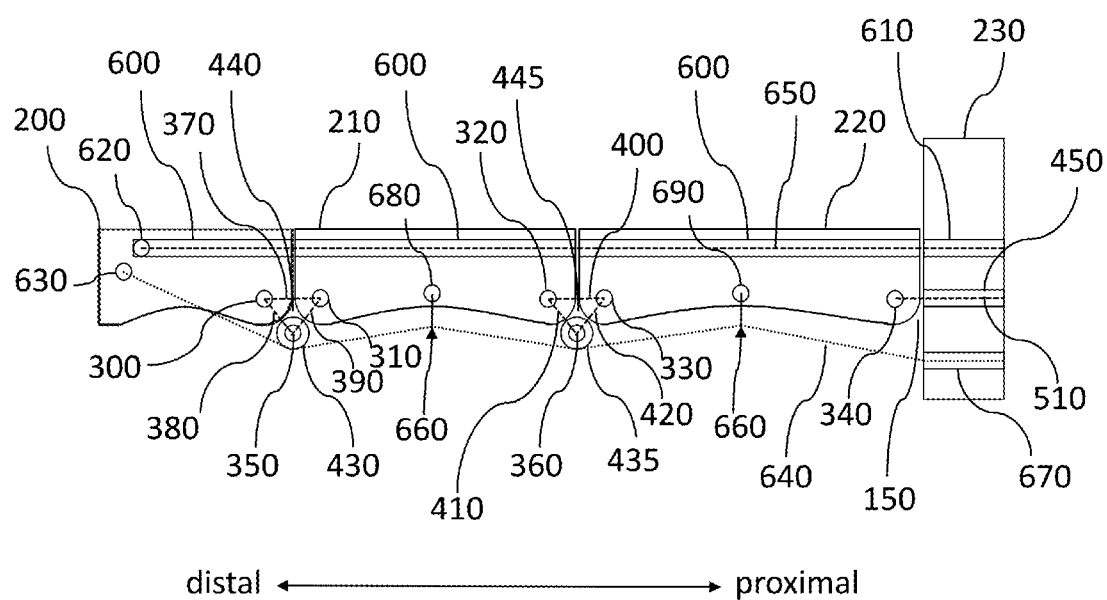
Figure 4 (mid-sagittal view)

JOINT AND DIGIT

CROSS REFERENCE TO RELATED APPLICATION

The present application claims the benefits of U.S. Provisional Application Ser. No. 61/777,024, filed Mar. 12, 2013, of the same title, which is incorporated herein by this reference in its entirety.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Contract No. 1R43HD070514-01 awarded by the National Institutes of Health.

TECHNICAL FIELD

This disclosure relates to the field of prosthetics, more specifically to a pinless anthropomorphic hinge or joint, and a digit comprising one or more phalanges connected by and articulating around pinless joints, whereby the joints provide compliant movement in more than one plane. This disclosure also relates to modular prosthetic systems comprising multiple digits, in particular for partial-hand replacements.

BACKGROUND

The following text should not be construed as an admission of knowledge in the prior art. Furthermore, citation or identification of any document in this application is not an admission that such document is available as prior art to the present disclosure, or that any reference forms a part of the common knowledge in the art.

A fundamental challenge in the field of prosthetic device development is to find a design that balances functionality with cost. The amputee desires a prosthetic device that both mimics and feels like the natural component that has been lost, for example, a finger or a hand. The replacement device must also be affordable. This need for cost effective prosthetic appliances is especially prevalent in poor countries and those suffering from civil war or natural disasters, such as Haiti or several African nations such as Sierra Leone, Uganda, and Kenya.

The human hand is an amazingly complicated feat of engineering, and very difficult to emulate. Even individual human fingers have an incredible range of motion and dexterity. This is especially evident when watching the fine motor skills of a sculptor, guitarist or surgeon. These motions are very difficult to mimic with an artificial device, especially in a cost-effective manner. In general, the engineering designs that most successfully mimic nature are also the most expensive. These designs can be described as "bionic", usually costing thousands of dollars to manufacture and maintain, or they are destined to remain relegated to the laboratory or to be used only by the most wealthy. The vast majority of people in need of affordable prosthetic devices lack the means to acquire these technologically sophisticated designs. Wonderful engineering feats in themselves, most bionic designs are not economically viable solutions for the masses. However, the other extreme is also lacking. More affordable prosthetic appliance designs tend to have short life spans, high failure rates, and are often expensive or difficult to maintain. From the amputee's perspective, these cheaper designs also tend to provide much less functionality and utility. It is one objective of the present disclosure to provide a prosthetic design that offers a balance of affordability and functionality.

A fundamental element of any prosthetic device that provides motion, for example an artificial arm, hand or finger, is a joint. Without one or more joints, a finger is simply a lever with severely limited functionality. Joints provide the means needed to flex or extend the digit, allowing for control to pick-up and grasp objects, ranging from such things as a hammer to a delicate wine glass.

Despite their importance, viable prosthetic joint designs are surprisingly limited, the vast majority relying on a pin that rigidly restricts motion to revolution about a single axis. Although simple in concept, "pin joints" do not mimic their natural counterparts, which are held together by a number of flexible ligaments. Knees, elbows, wrists, and fingers all rely upon ligaments for motion, typically biased to one plane but having some ability to move in all three spatial dimensions, including some rotational motion around an axis. Pins, on the other hand, limit motion to pure rotation, thus giving prosthetic appliances an artificial, rigid, and almost robotic motion.

Nevertheless, history has shown a propensity and preference for the pin (or screw, nail, rod, peg, or pinion). U.S. Pat. No. 1,608,689 (issued in 1926), describes an artificial hand comprising fingers and a thumb. The phalanges of each digit are held to their adjacent neighbors using pins.

U.S. Pat. No. 1,742,269 (1930) resorts to the same solution for providing a pivot point between opposing phalanges: pins.

Many more modern joint and prosthetic designs also use pins as the fundamental elements for providing motion between adjacent phalanges. Examples include: U.S. Pat. No. 5,326,369; U.S. Patent Application Publication No. 2004/0054424; U.S. Pat. App. Pub. No. 2006/0212129; U.S. Pat. No. 7,361,197; U.S. Pat. No. 7,655,051; U.S. Pat. App. Pub. No 2012/0203358.

Some different approaches do exist. An example from the WWII era is U.S. Pat. No. 2,500,614 which issued in 1948. This patent discloses a "ball and socket" system for the joints in an artificial hand. However, this solution poses significant manufacturing difficulties and is decidedly more complex in operation than simple pins.

Another prosthetic joints from this era is U.S. Pat. No. 2,549,074 which issued in 1951. Instead of pins, this patent discloses a joint comprising a flat metal sheet. This sheet connects the adjacent ends of the two phalanges. A space between the two phalanges allows the finger to flex into a closed position. Although different in concept than the more prominently used pin, this sheet metal joint still poses some of the same problems as the pin: it holds the adjacent phalanges rigidly fixed in all planes except that plane defined by flexion and extension.

Other prosthetic joints posing the same problems as highlighted above include U.S. Pat. No. 4,193,139, which discloses a pin-joint concept (1980) and U.S. Pat. No. 4,944,758, which discloses a ball-and-socket concept (1990).

All of these solutions tend to either limit motion to one plane, unlike natural joints, which allow some degree of motion in all three dimensions, including rotational movement around the digit's axis, or they require potentially more complicated and costly means for manufacturing and maintenance. It is the aim of this disclosure to overcome these problems, with a design that is simple, compact, waterproof, inexpensive, and easy to maintain.

SUMMARY

The present disclosure relates to novel and unique prosthetic joints, and digits comprising these joints. The joints are characterized by their unique lack of pins or nails to secure opposing ends of two phalanges together, and by the joint's ability to more accurately mimic the motion of a natural joint comprising ligaments, which allow some motion in all three dimensions. Instead of pins, the present disclosure secures adjacent phalanges using flexible cord that provides both mechanical integrity and strength, but also mimics natural ligaments by providing more natural movement in planes other than the primary plane defined by flexion and extension, including rotational motion around the axis defined by the extended digit. This "pinless" method of securing adjacent phalanges in a way that allows motion that more accurately mimics the motion of a natural human joint, is a novel and unobvious digit and/or phalanges prosthesis securement mechanism and presents a significant contribution to the field of prosthetics.

In one example of the present disclosure, a digit comprises three joints and three phalanges, the adjacent phalanges being secured using a triad of ligament wraps (loops) made from high-strength, low-creep, braided, polymer filament. For each joint, a single filament passes through a hole in a stabilizing cylinder and a hole in each adjoining phalanx (lever), making ten (10) alternating passes around the joint, with the filament ends secured to prevent loosening or slippage. While ten alternating passes are referenced, it will be appreciated that any number of passes may be used depending on the application. Multiple filament passes form a composite bundle having a tensile strength exceeding that of the phalanx material. This triad construction admits planar flexion-extension movement while limiting lateral, off-axis bending and axial twist to levels consistent with the anatomical finger. Some lateral bend and axial twist, this motion being called circumduction, are desirable as they help distribute tractive forces over the surface of objects, significantly increasing grasp quality.

These and other advantages will be apparent from the disclosure of the aspects, embodiments, and configurations contained herein.

As used herein, "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

It is to be noted that the term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

As used herein, "cylinder" is referred to as a hollow body comprising a circular cross section with parallel sides, slightly concave sides, or slightly convex sides. Therefore, a cylinder used herein, comprises a hole that passes through the circular cross-sectional area. In the present disclosure, a cylinder provides mechanical stabilization to the joint, and thus is also referred to as a stabilizing cylinder.

The term "extension" refers to when a digit is straight, under the influence of an extending force. As used herein, the term "flexion" refers to when any or all of the joints are rotated, putting the digit into a curl position under the influence of a flexing force.

As used herein, "loop" refers to a cord, filament, cable, wire, thread, line, yarn, string, or fiber, wherein the two ends of such a cord are secured into a circular loop. Alternatively, this cord, filament, cable, etc., may loop multiple times to form a composite loop. A loop simulates a ligament in the present disclosure.

The term "means" as used herein shall be given its broadest possible interpretation in accordance with 35 U.S.C., Section 112, Paragraph 6. Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves. As used herein, "phalange" refers to a phalangeal segment, phalanx, digit segment, or lever. So for the example of the human finger, a "phalange" refers to the proximal, intermediate and distal bones.

As used herein, "nip" refers to an empty space with its boundaries defined by the palmar or volar surfaces of two adjacent phalanges. By way of example, placing two rectangular blocks end-to-end provides no space between. However, rounding the palmar edges of the adjacent blocks provides space between two convex arcs. As used in the context of this disclosure, this space is referred to as a "nip".

As used herein, "plastic" refers to any of various organic compounds produced by polymerization, capable of being molded, extruded, cast into various shapes and films, or drawn into filaments used as textile fibers. A plastic can either be a thermosetting polymer or a thermoplastic polymer. Specifically, the plastic can include acetals, acrylics, acrylonitrile-butadiene-styrene, alkyds, coumarone-indene, diallyl phthalate, epoxy, fluoropolymer, melamine-formaldehyde, nitrile resins, nylon, petroleum resins, phenolics, polyamide-imide, polyarylates, polybutylene, polycarbonate, polyethylene, polyimides, polyphenylene oxide, polyphenylene sulfide, polypropylene, polystyrene, polyurethanes, polyvinyl acetate, styrene acrylonitrile, styrene butadiene latexes, sulfone polymers, thermoplastic polyester, unsaturated polyester, urea-formaldehyde, hexachloroethane, or a combination thereof. More specifically, the plastic can include polyethylene terephthalate (PET or PETE), high-density polyethylene (HDPE), low-density polyethylene (LDPE), polypropylene (PP), polystyrene (PS), nylon, or a combination thereof. The plastic can optionally include one or more additives. The term "plastic" should also be understood to include additives used to enhance the behavioral characteristics of the primary constituent material. Examples include glass fibers, carbon fibers, nanomaterials, hollow spheres, pigments, foaming agents, etc.

As used herein, "thermoset" refers to a polymer that solidifies or "sets" irreversibly when heated. Thermosets are valued for their durability and strength and are used primarily in automobiles and construction.

As used herein, "thermoplastic" refers to a polymer in which the molecules are held together by weak secondary bonding forces that soften when exposed to heat and return to its original condition when cooled back down to room temperature. When a thermoplastic is softened by heat, it can then be shaped by extrusion, molding or pressing. Examples of thermoplastics include polyethylene used in packaging, electrical insulation, milk and water bottles, packaging film, house wrap, and agricultural film; polypropylene used in carpet fibers, automotive bumpers, microwave containers, and external prostheses.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below. Also, while the disclosure is presented in terms of exemplary embodiments, it should be appreciated that individual aspects of the disclosure can be separately claimed.

BRIEF DESCRIPTION OF DRAWINGS

The accompanying drawings are incorporated into and form a part of the specification to illustrate examples of the aspects, embodiments, or configurations disclosed herein. These drawings together with the description, explain the principle of the aspects, embodiments, or configurations. The drawings simply illustrate preferred and alternative examples of how the aspects, embodiments, or configurations can be made and used and are not to be construed as limiting the aspects, embodiments, or configurations to only the illustrated and described examples. Further features and advantages will become apparent from the following, more detailed, description of the various aspects, embodiments, or configurations, as illustrated by the drawings referenced below.

FIG. 1 is a front elevation view of one embodiment of the present disclosure, of a joint of a single loop.

FIG. 2 is a front elevation view of one embodiment of the present disclosure of a joint of three loops.

FIG. 3 is a front elevation view of one embodiment of the present disclosure of a digit of three levers, three hinges and a base.

FIG. 4 is a front elevation view of one embodiment of the present disclosure of a digit of three levers, three hinges, and a base.

DESCRIPTION OF EMBODIMENTS

Figure 5:
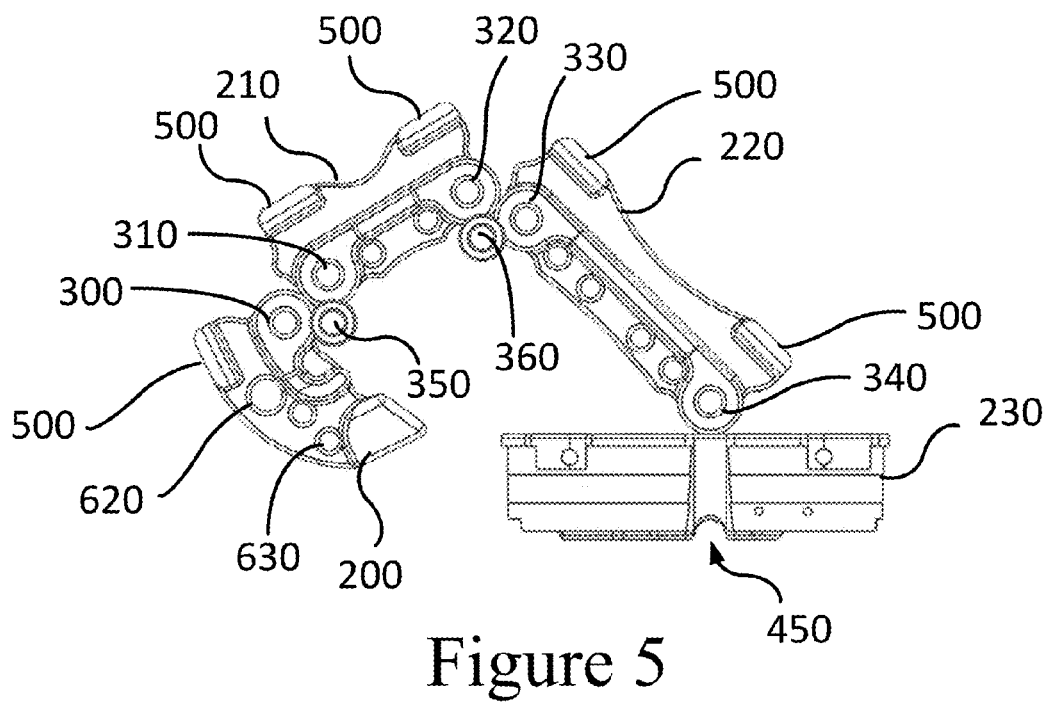
FIG. 5 is a front elevation view of one embodiment of a digit of the present disclosure.

The following detailed description illustrates the disclosure by way of example and not by way of limitation. This description will clearly enable one skilled in the art to make and use the disclosure, including what is presently believed to be the best mode of carrying out the disclosure.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The present disclosure relates to novel and unique prosthetic joints, and digits comprising these joints, as well as modular prosthetic systems comprising multiple digits, in particular for partial-hand replacements. The joints are characterized by their unique lack of pins, screws or nails to secure opposing ends of two phalanges together, and by the joint's ability to more accurately mimic the motion of a natural joint comprising ligaments, which allow some motion in all three dimensions, a capability called digit circumduction. Instead of pins, the present disclosure secures adjacent phalanges using flexible cord that provides both mechanical integrity and strength, but also mimics natural ligaments by providing more natural movement in planes other than the primary plane defined by flexion and extension, including rotational motion around the axis defined by the extended digit.

Turning to FIG. 1, some embodiments of the present disclosure is a joint comprising a first distal lever 100 and a second proximal lever 110, in which the two levers are aligned lengthwise along a first reference axis, the horizontal X-axis. Each lever comprises a proximal and a distal ends. The joint connects the proximal end of the first lever to the adjacent distal end of the second lever. The levers are also defined by the vertical Y-axis, and the axis orthogonal to the X- and Y-axis, the Z-axis. The upper surface of the levers, in the Y-axis, is defined as the dorsal side. The lower surface of the levers, also in the Y-axis, is defined as the palmar side. The palmar sides of the adjacent ends of the two levers are both rounded, across their entire width in the Z-axis direction. Rounding these edges allows for smooth, natural movement when the joint is flexed or extended. Rounding the two opposing edges also forms a space on the palmar side, between the two adjacent levers. This space, referred to as a "nip" 150 has boundaries defined by the rounded edges, which form adjacent convex arcs. The two opposing arcs move against each other when the joint flexes and extends.

The distal lever 100 contains a first hole 120 that passes through its width in the Z-axis direction. This hole is preferably located in the proximal end and the palmar half of the first lever. Similarly, the second lever 110 also has a hole 130, with this second hole also passing through the second lever's width in the Z-axis direction. The second hole is preferably located in the distal end and the palmar half of the second lever. The two holes, like the two levers, preferably lay adjacent two each other at about the same height in the Y-axis direction.

The two holes in conjunction with a loop 140, secure the adjacent levers together, much like ligaments in a natural joint. The loop 140 comprising a cord, line, filament, etc., passes through the two holes, forming a complete circular loop that provides the structural stability required of a joint, but also allows for the biased movement in the XY-plane for flexion and extension. However, unlike pin joints, the loop also provides some flexibility, much like a ligament, to provide some degree of motion in the other dimensions, for example in the YZ and XZ-planes, as well as some rotational motion along the X axis.

In some embodiments of the present disclosure, the joint provides biased movement in the same direction and plane as the natural appendage being replaced. So by example, a joint for a prosthetic replacing a finger, will provide biased movement in the XY-plane, whereby flexing will pull the finger downward in the palmar direction, and extension will release the finger back in the dorsal direction.

In some embodiments, the joint limits motion in the XZ-plane to less than 1, 2, 3, 4, or 5 degrees. In some embodiments, the joint limits motion in YZ-plane to less than 1, 2, 3, 4, or 5 degrees.

In some embodiments, the joint limits axial rotation around the X-axis to less than 20, 19, 18, 17, 16, 15, 14, 13, 12, 11, 10, 9, 8, 7, 6, 5, 4, 3, 2, or 1 degree in either or both the clockwise or counter-clockwise directions.

In some embodiments the levers 100, 110 and the loop 140 are constructed of metal, plastic, ceramic, carbon fiber or a combination thereof. The materials of construction may be the same for all of the components comprising the joint, or each individual element may be constructed from its own unique material, different from the materials chosen for any other element comprising the joint.

In some embodiments the loop comprises 80# Test, Spectra® by Honeywell, or materials by Innovative Textiles, Inc., or a combination thereof.

In some embodiments of the present disclosure, the levers 100, 110 may be plastic.

In some embodiments of the present disclosure, the levers may be produced by injection molding.

In some embodiments of the present disclosure, the loop 140 may comprise plastic, ceramic, carbon fiber, metal wire, or a combination thereof.

In some embodiments of the present disclosure, the loop 140 comprises a single circular strand, cord, filament, etc. In some embodiments the loop comprises more than one circular strand, cord, filament, etc., with each cord passing through both holes of the joint. The number of passes used depends on the strength and structural requirements of the joint being designed and would be known to one skilled in the art.

In some embodiments the material of construction for the levers 100, 110 comprises aluminum.

Referring to FIG. 2, in some embodiments of the present disclosure, the joint further comprises a stabilizing cylinder 180 that is placed in the nip 150 located on the palmar side of the adjacent ends of the two levers 100, 110. This stabilizing cylinder 180 fits in the space formed by the rounded edges of the two levers, and lays in the Z-axis direction. The width of the stabilizing cylinder 180 may be about the same as the width of the levers 100, 110 in the Z-axis direction, but may also be a little narrower or a little wider. The two ends of the stabilizing cylinder 180 may be flanged to assist with holding the stabilizing cylinder 180 in the nip 150 (see for example the first flange 505 and second flange 507 shown in FIGS. 6, 7, 10 and 13). The stabilizing cylinder 180 comprises a hole 190 that passes through the length of the stabilizing cylinder 180 in the Z-axis direction. The stabilizing cylinder's 180 diameter may be such that it provides enough mass to provide the structural support needed, but is not so large as to impede the joint's motion.

In some embodiments the stabilizing cylinder 180 is held in position, by securing a second loop 160 though the first lever's hole 120 and the hole 190 passing through the stabilizing cylinder 180, as well as a third loop 170 secured through the second lever's hole 130 and the hole 190 passing through the stabilizing cylinder 180. This results in a triangular formation of loops, or triad 195, when viewing the joint from the side. This triple system of loops and a stabilizing cylinder 180 provides additional stability to the joint, in particular by limiting rotational movement around the X-axis. These additional loops (160 and 170), and the stabilizing cylinder 180, like the first loop 140 and the levers (100 and 110), are constructed of metal, plastic, ceramic, carbon fiber or a combination thereof.

Turning to FIG. 3, in some embodiments of the present disclosure is a digit, comprising a first lever 200, a second lever 210 and a third lever 220, corresponding to a distal, intermediate and proximal phalange respectively. The three levers are preferably aligned lengthwise along the X-axis, and each lever comprises a proximal end and a distal end. The proximal end of the first lever is adjacent to the distal end of the second lever, the proximal end of the second lever is adjacent to the distal end of the third lever, and the proximal end of the third lever is adjacent to the base. The first hole 300 of the first 200 lever is preferably located in the proximal end of the first lever, the second hole 310 of the second lever 210 is preferably located in the distal end of the second lever, the third hole 320 of the second lever 210 is preferably located in the proximal end of the second lever, the fourth hole 330 of the third lever 220 is preferably located in the distal end of the third lever, and the fifth hole 340 of the third lever 220 is preferably located in the proximal end of the third lever.

All five holes are preferably located in the palmar half of their respective levers, and all five holes pass through the width of their respective levers in the Z-axis direction, and all are preferably aligned at about the same height in the Y-axis direction.

The proximal and palmar end in the Z-axis direction of the first lever 200 is rounded. The proximal and distal palmar ends, in the Z-axis direction, of both the second lever 210 and the third lever 220 are rounded.

The adjacent, rounded ends of the proximal end of the first lever 200, and distal end of the second lever 210 form a first nip 440, and the rounded sides of the adjacent second lever 210 and third lever 220 form a second nip 445.

In some embodiments the digit forms a first joint that secures the first lever 200 to the second lever 210 by placing a first stabilizing cylinder 430 in the first nip 440 and securing a first loop 370 through the first hole 300 of the first lever 200 and the second hole 310 of the second lever 210, securing a second loop 380 through the first hole 300 of the first lever 200 and the stabilizing cylinder's hole 350, and securing a third loop 390 through the second hole 310 of the second lever 210 and the stabilizing cylinder's hole 350.

The digit further comprises a second joint that secures the second lever 210 to the third lever 220 by placing a second stabilizing cylinder 435 in the second nip 445 and securing a fourth loop 400 through the third hole 320 of the second lever 210 and the fourth hole 330 of the third lever 220, securing a fifth loop 410 through the third hole 320 of the second lever 210 and the second stabilizing cylinder's hole 360, and securing a sixth loop 420 through the fourth hole 330 of the third lever 220 and the second stabilizing cylinder's hole 360.

Referring again to FIG. 3, in some embodiments the digit further comprises a third joint that secures the third lever 220 to a base 230. The base 230 comprises an anchor 450, which in some embodiments is a hole or slot that passes through the base in the X-axis direction. The anchor 450 is at about the same height in the Y-axis direction as the fifth hole 340. An attachment 510 secures the third lever 220 to the base 230 by passing the attachment 510 through the fifth hole 340 and the anchor 450.

In some embodiments all three joints of FIG. 3 provide biased motion in the palmar direction in the XY-plane, and also provide some motion in the dorsal direction of the XY-plane, some motion YZ-plane, some motion in the XZ-plane, as well as rotational motion around the X-axis.

In some embodiments all three joint of FIG. 3 limit motion in the XZ-plane to less than 1 degree, 2, 3, 4, or 5 degrees. In some embodiments the joint limits motion in the YZ-plane to less than 1 degree, 2, 3, 4, or 5 degrees.

In some embodiments of the present disclosure, the levers are plastic.

In some embodiments of the present disclosure, the levers and base are produced by injection molding.

Turning to FIG. 4, some embodiments contain a tension guide 600. This guide may comprise a notch, indentation or other suitable means located in the dorsal half of each lever, wherein the tension guide is oriented in the X-axis direction. Through the tension guide 600, runs a tension cord 650, wherein the tension cord 650 is anchored on the proximal end of the digit with the base 230, by a tension restraint 610, and wherein the tension cord 650 is anchored on the distal end of the digit by securing the tension cord 650 in tension hole 620, this tension hole located in distal third of the first lever 200, also in the dorsal half of the first lever 200, in the Y-axis direction. The tension guide 600 and tension cord 650 run through the entire length in the X-axis direction of the second lever 210 and third lever 220. As stated, the tension guide starts at the proximal end of the first lever 200 and terminates at the tension hole 620. This arrangement provides a constant force that pulls the digit, via the tension cord 650, into the fully extended position.

The tension cord may comprise any suitable elastomer. Examples include but are not limited to elastic bands and bungee cord. The length required to provide a suitable force, is not elaborated here, and that design feature is known to one of skill in the art. The tension cord may also comprise a filament and spring acting in series, or a single spring.

Referring to FIG. 4, in some embodiments an eighth hole 680 is located about midway in the length of the second lever 210, in the palmar half of the second lever 210. A similar hole, the ninth hole 690, is located about midway in the length of the third lever 220, also in the palmar half of the third lever 220. Through the eighth hole 680 and ninth hole 690 are placed loops referred to as actuator guides 660. The actuator guides 660, guide an actuator cord 640 to which the amputee applies force, against the force exerted by the tension cord 650, to flex the digit. The actuator cord 640 is firmly secured through an actuator hole 630, located in the distal end, at about midline in Y-axis direction, of the first lever 200. The actuator cord 640 then passes over the first stabilizing cylinder 430 of the first joint connecting the first lever 200 to the second lever 210, passes through the actuator guide 660 of the second lever 210, over the second stabilizing cylinder 435 of the second joint connecting the second lever 210 to the third lever 220, passes through the actuator guide 660 of the third lever 220, and finally passes through the actuator lead 670 located in the base 230.

In some embodiments the actuator guides 660, like the loops used to construct the joints, may be made of plastic, carbon fiber, metal, ceramic or a combination thereof.

In some embodiments the actuator cord is preferably a non-elastic cord, cable, wire, any other suitable non-elastic cord means, or a combination thereof.

In some embodiments the relative lengths of the distal, intermediate, and proximal levers match the natural proportions of a human finger.

Figure 6:
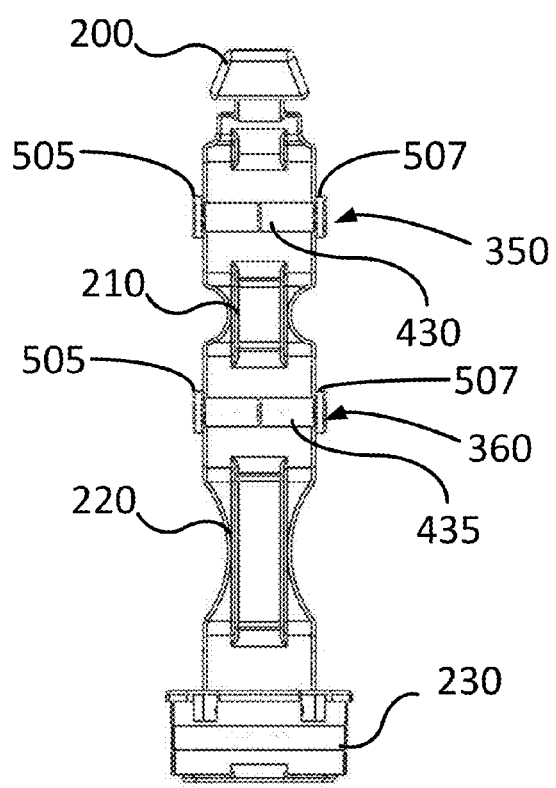
FIG. 6 is a bottom plan view of one embodiment of a digit of the present disclosure.
Figure 7:
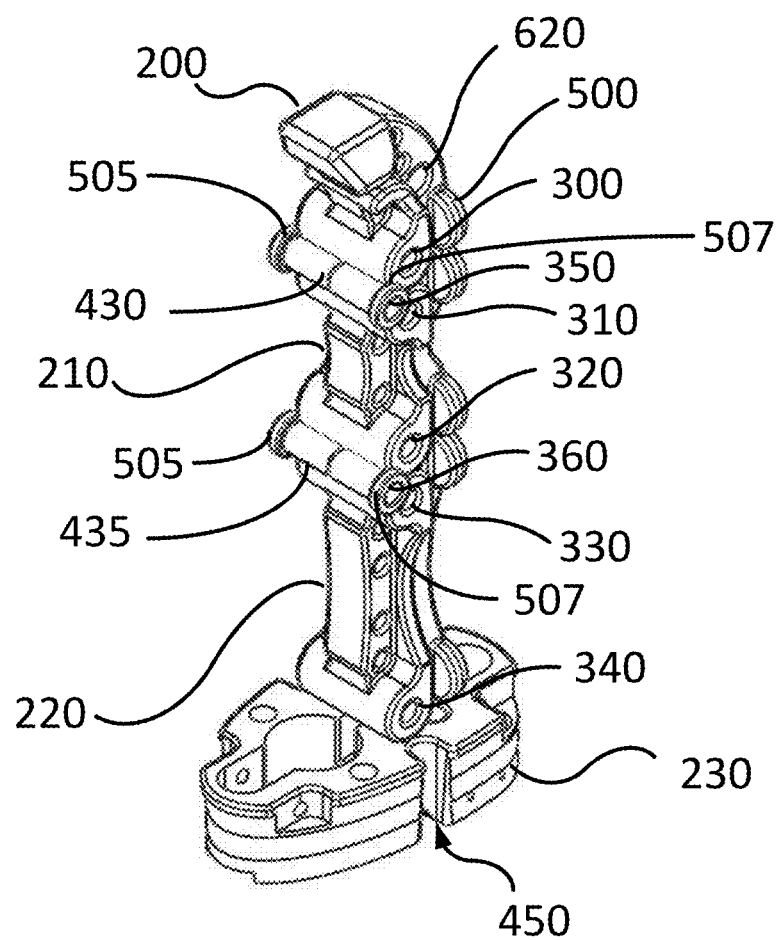
FIG. 7 is a perspective view of one embodiment of a digit of the present disclosure.
Figure 8:
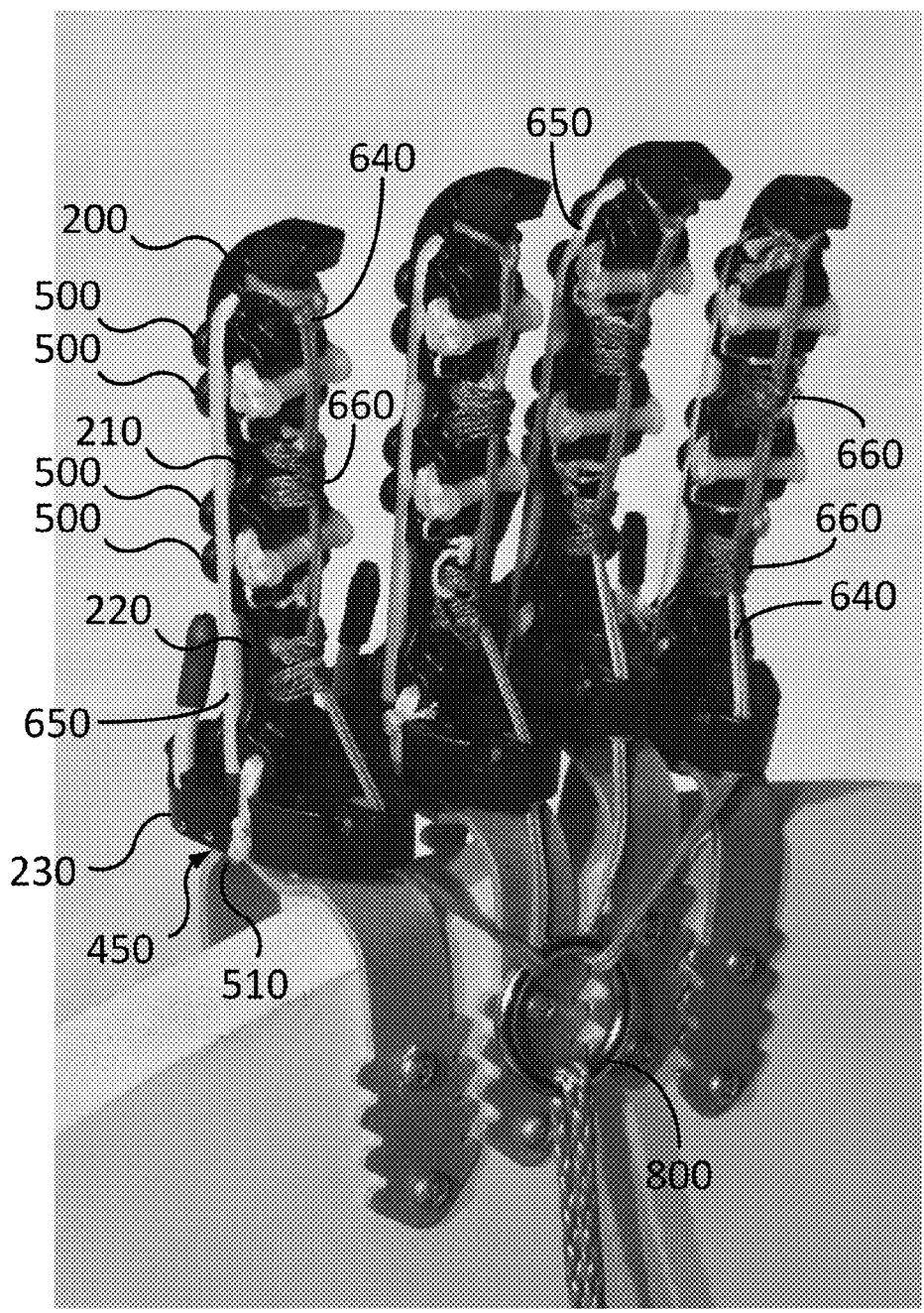
FIG. 8 is a perspective photograph of an actual prototype of the present disclosure, of four digits that comprise a partial hand amputation prosthetic device.
Figure 9:
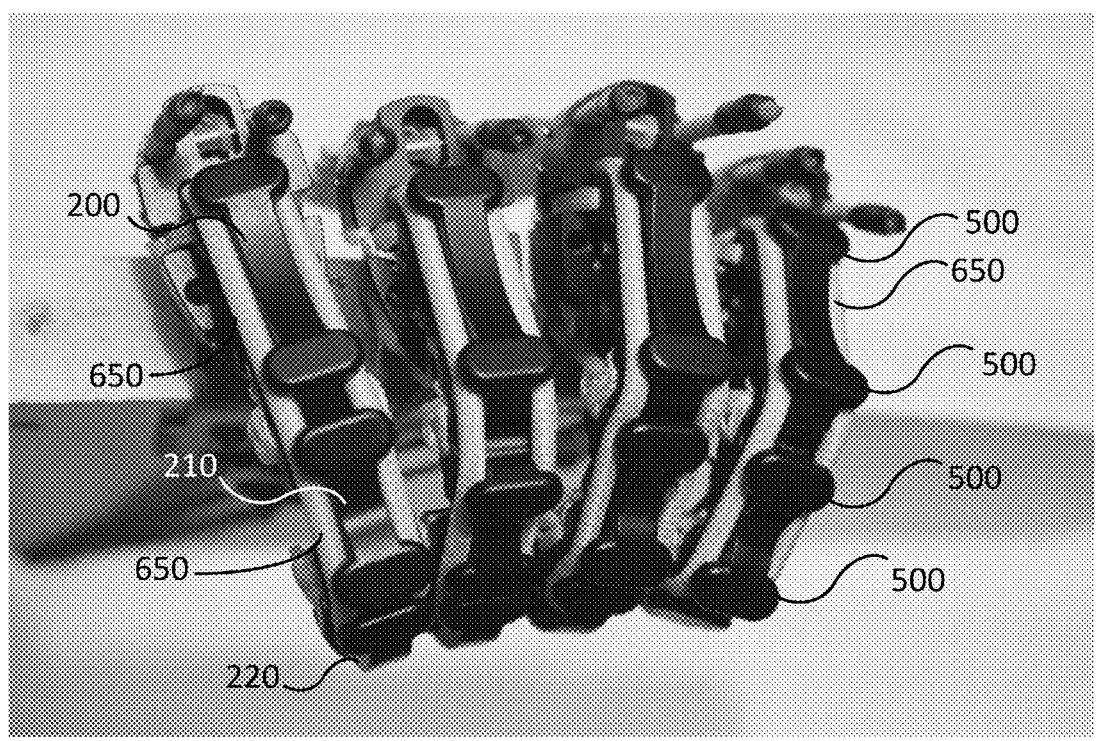
FIG. 9 is a perspective view photograph of an actual prototype of the present disclosure, of four digits in flexion.
Figure 10:
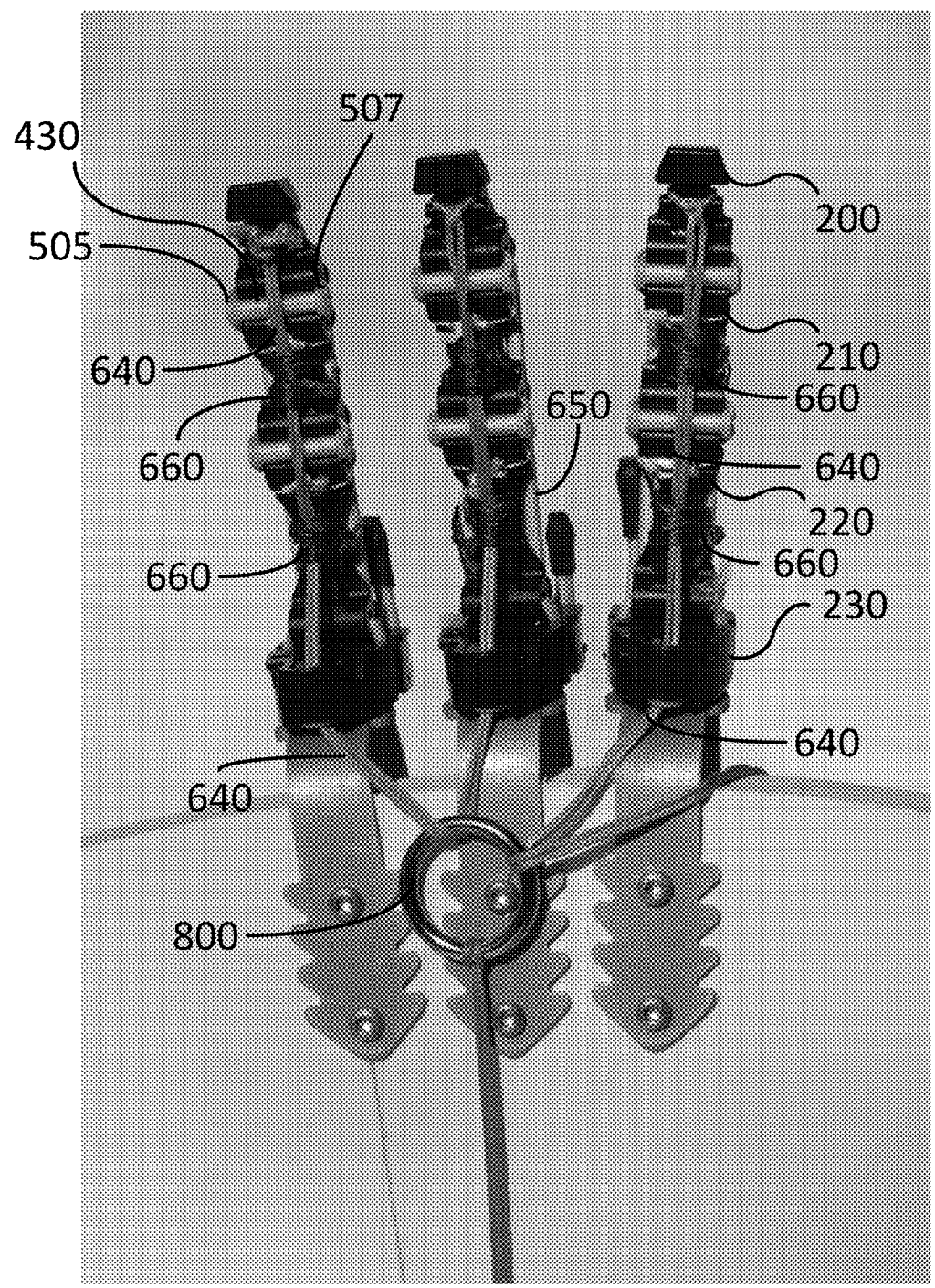
FIG. 10 is a bottom plan view photograph of an actual prototype of the present disclosure, illustrating an actuating cord and ring for flexing the digits.
Figure 11:
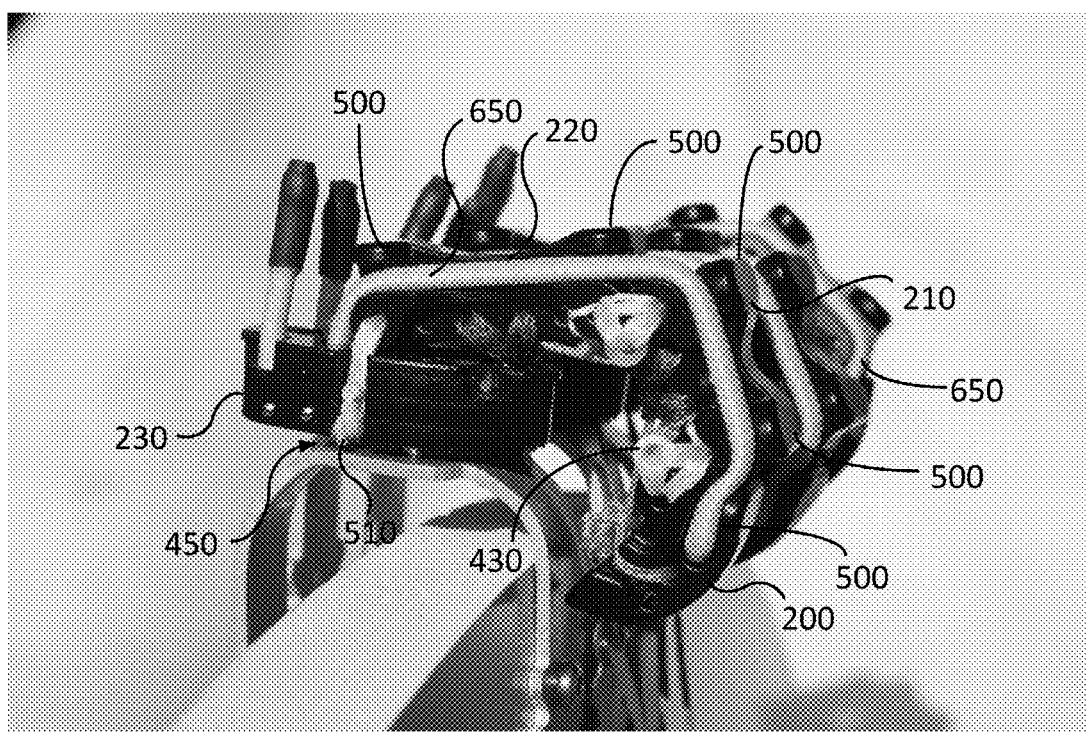
FIG. 11 is a front elevation view photograph of an actual prototype of the present disclosure, of four digits in flexion.
Figure 12:
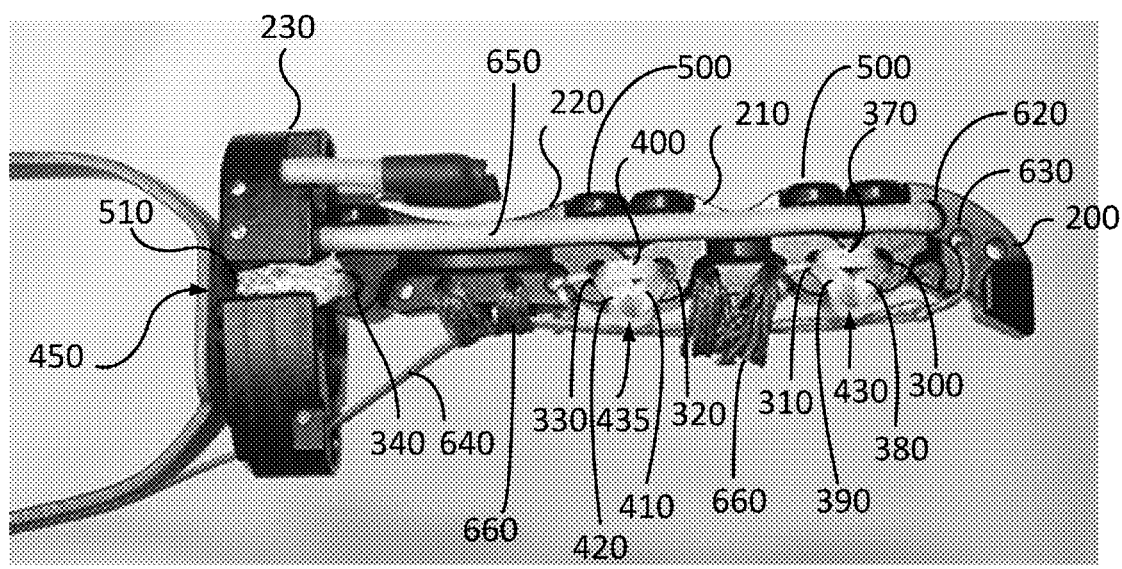
FIG. 12 is a front elevation view photograph of an actual prototype of the present disclosure, of a single digit in full extension.
Figure 13:
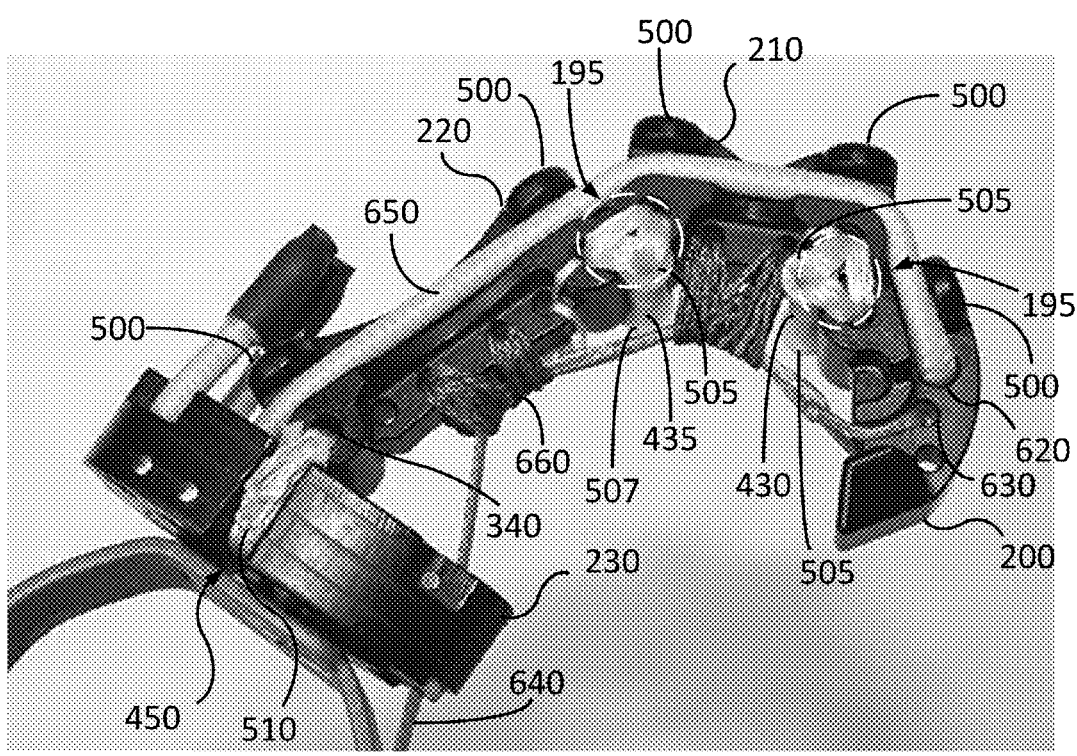
FIG. 13 is a front elevation view photograph of an actual prototype of the present disclosure, of a single digit in partial flexion.
Figure 14:
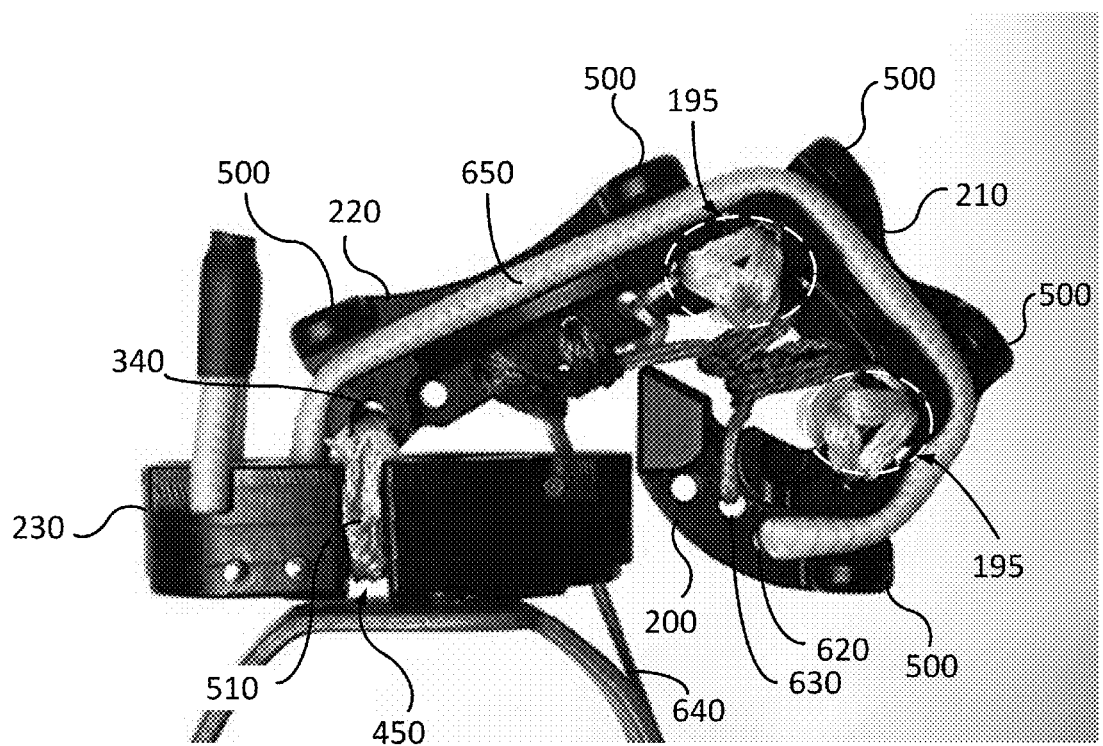
FIG. 14 is a front elevation view photograph of an actual prototype of the present disclosure, of a single digit in full flexion.

FIGS. 5-14 show different views of the prosthesis of this disclosure. FIGS. 5-6 are side and end views, respectively, of the prosthesis in full flexion. FIG. 7 is a perspective view of the prosthesis in an extended position. Flanges 500 on each of the first and second levers 100 and 110 include flanges 500 to hold the tension cord 650 in position during digit and phalanges movement. FIG. 8 depicts four digits joined using a slip ring arrangement. The slip ring arrangement includes a ring 800 connected to multiple actuator cords 640, each of which independently operates a corresponding digit. FIG. 9 shows four digits in flexion showing bases inclined with respect to the palm to achieve spherical prehension. FIG. 10 shows three digits joined using a slip ring engagement. FIG. 11 shows three digits in flexion. The prosthesis replicates many of the elements of an anatomical hand. FIG. 12 shows a biomimetic digit in full extension. FIG. 13 shows a biomimetic digit in partial flexion. Finally, FIG. 14 shows a biomimetic digit in full flexion.

EXPERIMENTAL

The following examples are provided to illustrate certain aspects, embodiments, and configurations of the disclosure and are not to be construed as limitations on the disclosure, as set forth in the appended claims. All parts and percentages are by weight unless otherwise specified.

In one example, the three joints of a digit use a triad of ligament wraps (loops) made from high-strength, low-creep, braided Spectra® filament (80 lbf test×0.016" diameter, Innovative Textiles, Inc.) originally developed for competitive sport fishing. A single filament passes through holes in the stabilizer (cylinder) and each adjoining phalanx (lever), making ten (10) alternating passes around the joint, and its ends are secured to prevent loosening or slippage. Multiple filament passes form a composite bundle having a tensile strength exceeding that of the phalanx material. This triad construction admits planar flexion-extension movement while limiting lateral, off-axis bending and axial twist to levels consistent with the anatomical finger. Some lateral bend and axial twist are desirable as they help distribute tractive forces over the surface of objects, significantly increasing grasp quality. This configuration is called "digit circumduction" in the anatomical hand and not currently in use in any other existing articulating digits or multi-articulating hands—body-powered or otherwise—that allow for beneficial digit circumduction.

Two passes of nylon-jacketed elastic "bungee" cord on each digit's dorsal side act as extensors (tension cord). Their tension level is adjusted to overcome cosmetic cover stiffness and flexor tendon drag to ensure full digit extension. Two passes of Spectra® cord (150 lbf test×0.025" diameter, Ashaway, Inc.), specially braided for professional kite fighting and sporting equipment, form the flexor tendon on the digit's volar side. Entering the digit through a special low-wear ceramic textile guide in the base, this flexor tendon (tension cord) bridges the proximal and middle phalanges and attaches directly to the distal phalanx. Tendon guides (tension guides) made from open coils of Spectra® filament (100 lbf test×0.022" diameter, Innovative Textiles, Inc.) attach to the proximal and middle phalanges (levers), analogous to the annular and cruciform fibrous sheaths that transfer force to the phalangeal segments in the anatomical finger. These guides also minimize frictional drag on the tendon (actuator cord) analogous to the synovial sheath. Adjusting the length and attachment locations of these "synovial coils" on each phalanx controls the sequencing of joint movements as the digit flexes.

The prosthesis design of this disclosure intentionally permits selection of attachment points that initiate flexion at the base of the digit and then move proximally from the distal phalanx. If an object is not encountered as the digit sweeps, it closes to establish "key grip" against an opposition thumb, one of the most important and useful prehension patterns. If an object is encountered during sweep, digit flexion begins at the distal end, curling back against the object and drawing it towards the base for strong, stable grasp.

To facilitate low-cost manufacture, strict injection molding criteria were imposed on the base and phalange designs to use standard two-part "mud" bases without expensive secondary slides. The parts are also designed for "family molding" in one injection cycle to maximize manufacturing efficiency and minimize material waste per shot. The net result is a considerable reduction in tooling and final part cost. For this effort, parts were fabricated by the FirstCut® division of ProtoMold® from Delrin® 150 acetal homopolymer (DuPont) using state-of-the-art high-speed conventional machining optimized for rapid prototype fabrication. While cost effective within the scope of this developmental work, part pricing for components fabricated this way is not viable for long-term commercial production.

At least three distinct digit lengths are needed to avoid "broom hand" (i.e., all digits mounted on a straight knuckle line and having the same length—like a broom.) These phalangeal segments permit various combinations to obtain different overall digit lengths without additional tooling cost or complexity. The distal phalanx serves as digit tip with articulation on its proximal end only, along with flexor tendon and extensor attachment points; it is common to all sizes. Table 1 shows possible constructions.

TABLE 1

Possible Overall Digit Lengths Based on Phalanx Combinations

| Phalanx | Length | Index (2)[†] & Ring (4) | Middle (3) | Small (5) |
| --- | --- | --- | --- | --- |
| Proximal | 1.13 in | x1 | x2 | |
| Middle | 0.75 in | x1 | | x2 |
| Distal | 0.62 in | x1 | x1 | x1 |
| Digit Length | | 2.50 in | 2.88 in | 2.12 in |

[†]Thumb is traditionally numbered digit 1.

The digit mounting means disclosed herein can better serve partial hand amputees. Instead of a single composite "rack" that forces digits into an unnaturally straight line as currently used in existing products, the digit mounting means of this disclosure can provide a more versatile strap system offering several advantages. Each digit is mounted on a single metal structural strap folded into a saddle or "taco" shape that is affixed on both the volar and dorsal aspects of a partial-hand prosthetic shell for increased strength and rigidity. Each strap's ends are designed with serrations that allow it to be strongly secured using standard fiberglass or carbon fiber layup techniques commonly employed in the field; holes are provided for tinner's rivets if preferred (another common attachment method.) Each strap is independently shapeable by the prosthetist to position each digit optimally on an arc within the anatomical hand space rather than forcing them into an artificial, non-optimal line. As the straps are rigidly integrated into the prosthetic shell and cannot be easily removed, the digit bases are designed to attach with a screw accessible from the front, permitting easy modular replacement if necessary. Moreover, the flexion plane of each digit can be oriented independently with respect to the palm for improved spherical prehension. This innovation can markedly benefit amputees having excessive scarring, adipose tissue, bulbous amputations, or where the prosthetist must orient digit movements to optimally interface with remaining anatomical digits for coordinated useful grasp.

TABLE 2

Laboratory Testing Results

| | | |
| --- | --- | --- |
| Physical Parameters | Moving Length | 2.88 inches |
| | Total Weight | 1.0 ounce (including strap mount) |
| | Full Curl Tendon Tension | 7.5 lbf (no load, clear swing trajectory) |
| | Full Curl Tendon Excursion | 1.4 inches (no load, clear swing trajectory) |
| | Lateral Circumduction Angle | 5.7° (0.25 inch tip displacement off midline) |
| | Axial Twist Angle | ±18° on axis |
| Laboratory Performance | Max Lift Load: "Hook Grip" | 20 lbf (1.0 inch diameter handle) |
| | Sustaining Tendon Tension | 27 lbf (forward force ratio [FFR]: 0.74) |
| | Max Tip Force: "Key Grip" | 3.1 lbf (at extreme digit tip) |
| | Sustaining Tendon Tension | 12.0 lbf (FFR: 0.26) |
| | Max Reverse Bending Load | 12 lbf (at extreme digit tip) |
| | Flexion Cycle Life to 1st Failure | 637K tendon failure, replaced & continued |
| | Extended Cycle Life | >1.1 MM test terminated, no failure |

To ensure "worst case" cantilever loading conditions, laboratory testing was carried out using the middle digit configuration given in Table 1; test results are outlined in Table 2. Hook and key grip prehension forces were chosen for measurement as these patterns are less subjective and 1) are relatively easy to instrument, 2) rely directly upon the digit mechanism itself, and 3) don't depend upon the object being grasped, its orientation, cosmetic cover characteristics, etc.

To perform cycle life testing, a dedicated-purpose apparatus was constructed. Destructive cycle testing showed units attaining an average of 637K grasping cycles before tendon failure. Replacing the tendon is trivial; in one case this was done and testing extended. In this case, all other structures of the digit—excluding the tendon—survived in excess of 1.1 MM cycles before testing was terminated. Measurements of lateral bending tip displacement and axial twist taken before and after cycling showed no change (0.25" off midline and ±18° on-axis twist, respectively) indicating the ligament wrap triads did not stretch or loosen during the test. Subsequent teardown and examination in the laboratory found minor compression set but no fraying of the ligament wraps in contact with the phalanges, mild localized polishing on phalanx articulation surfaces, and some transfer of tendon material to the inside of the synovial coil guides (accounting for the tendon's failure); no other discernible wear was found.

Configured as a Gang-of-Four (a full partial-hand prosthesis), best operation was achieved joining digits as pairs and passing their common flexor tendon through a low-friction slip ring. This arrangement behaves similar to a conventional whiffle tree, equilibrating flexion and grasping force, but with less excursion loss. Additional development is required to implement a commercially viable whole-hand design. Several lessons were learned during the work outlined above:

(1) Replicating structural elements of the anatomical finger to create a biomimetic prehensile digit having comparable appearance, movement, and prehension force envelope is possible.

(2) Synthetic filaments can perform analogous to the ligaments, tendons, fibrous sheaths, and synovial sheaths found in the anatomical digit, achieving excellent service life while simultaneously reducing cost, weight, mechanical complexity, and eliminating the need for lubrication.

(3) The triad ligament wrap construction described here achieves outstanding articulation stability and limits both lateral bending and axial twist to acceptable levels.

(4) Allowance for limited lateral bending and axial twist enhances the digit's ability to adaptively grasp by permitting surface contact forces and joint torques to equilibrate.

(5) Incorporating digits into assistive appliances as separate components—not grouped onto a common rack or bar—enables the prosthetist to better position the digits within the anatomical hand space for optimal grasping function and cosmesis.

(6) A quasi-whiffle tree connection for multiple digit flexor tendons (i.e. a slip-ring arrangement) provides a reasonable balance of flexor tendon excursion and force for each digit.

A number of variations and modifications of the disclosure can be used. It would be possible to provide for some features of the disclosure without providing others.

For example in one alternative embodiment, the holes 120 and 130 pass along the X-axis at least substantially through the first distal lever 100 and second proximal lever 110. In this manner, the looped cord passes through each of the adjoining first distal and second proximal levers rather than through the sides of the first distal and second proximal levers as shown in FIG. 1.

The present disclosure, in various aspects, embodiments, and configurations, includes components, methods, processes, systems and/or apparatus substantially as depicted and described herein, including various aspects, embodiments, configurations, subcombinations, and subsets thereof. Those of skill in the art will understand how to make and use the various aspects, aspects, embodiments, and configurations, after understanding the present disclosure. The present disclosure, in various aspects, embodiments, and configurations, includes providing devices and processes in the absence of items not depicted and/or described herein or in various aspects, embodiments, and configurations hereof, including in the absence of such items as may have been used in previous devices or processes, e.g., for improving performance, achieving ease and\or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more, aspects, embodiments, and configurations for the purpose of streamlining the disclosure. The features of the aspects, embodiments, and configurations of the disclosure may be combined in alternate aspects, embodiments, and configurations other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed aspects, embodiments, and configurations. Thus, the following claims are hereby incorporated into this Detailed Description, with each claim standing on its own as a separate preferred embodiment of the disclosure.

Moreover, though the description of the disclosure has included description of one or more aspects, embodiments, or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed:

1. A method for stabilizing and controlling an external prosthetic biomimetic digit, the method comprising: contacting a proximal end of a first phalange with an adjacent distal end of a second phalange, wherein a palmar side of the proximal end of the first phalange is rounded to form a first arc, and a palmar side of the distal end of the second phalange is rounded to form a second wherein the first arc and the second arc form a nip; positioning a stabilizing cylinder in the nip; and attaching the proximal end of the first phalange to the adjacent distal end of the second phalange using a flexible triangular formation of a first loop, a second loop, and a third loop, the attaching comprising: a first securing comprising securing the first loop through a first hole positioned towards the proximal end and the palmar side of the first phalange, and securing the first loop through a second hole positioned towards the distal end and the palmar side of the second phalange; a second securing comprising securing the second loop through the first hole and the stabilizing cylinder; and a third securing comprising securing the third loop through the second hole and the stabilizing cylinder, wherein: the triangular formation allows movement of the first phalange and the second phalange to a first movement between an extended position and a flexed position, the first movement is substantially within a first plane, the extended position is substantially aligned with an axis which is parallel to the long axis of the joint and positioned within the first plane, the first arc and the second arc move against each other during the first movement, and the first hole and second hole pass through the first phalange and the second phalange, respectively, substantially perpendicular to the first plane.

2. The method of claim 1, wherein the stabilizing cylinder comprises:
 a first end and a second end;
 a first flange positioned at the first end; and
 a second flange positioned at the second end.

3. The method of claim 1, wherein the first phalange and the second phalange allow: a secondary second movement of less than 5 degrees a second plane substantially perpendicular to the first plane; and a third movement that is rotational around the axis of less than 20 degrees, wherein: the third movement is in at least one of a clockwise direction or a counter-clockwise direction around the axis.

4. The method of claim 1, further comprising securing a proximal end of the second phalange to a base.

5. The method of claim 4, wherein the securing the proximal end of the second phalange to the base comprises securing a fourth loop through a third hole positioned towards the proximal end and the palmar side of the second phalange and a fourth hole positioned in the base.

6. The method of claim 5, further comprising applying an extending force along the axis, wherein the applying an extending force comprises:
 positioning a tension cord in a first tension guide positioned along a dorsal side of the first phalange;
 positioning the tension cord in a second tension guide positioned along the dorsal side of the second phalange;
 securing a first end of the tension cord towards a distal end and the dorsal side of the first phalange; and
 securing a second end of the tension cord to the base, wherein the securing the first end of the tension cord and the securing the second end of the tension cord results in the extending force.

7. The method of claim 6, further comprising:
securing a first end of a cord towards the distal end of the first phalange; wherein:
the cord is configured to apply a flexing force to the distal end of the first phalange towards the base,
the cord is positioned along the palmar side of the first phalange and the palmar side of the second phalange, and
the cord passes over the stabilizing cylinder.

8. The method of claim 7, wherein:
when applying a flexing force that is less than or equal to the extending force, the first phalange and the second phalange are in the extended position, and
when applying the flexing force that is greater than the extending force, the first phalange and the second phalange are in the flexed position.

* * * * *